United States Patent
Shimura

(10) Patent No.: US 8,194,969 B2
(45) Date of Patent: *Jun. 5, 2012

(54) METHOD AND APPARATUS FOR VISUAL INSPECTION

(75) Inventor: Kei Shimura, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 32 days.

This patent is subject to a terminal disclaimer.

(21) Appl. No.: 12/751,723

(22) Filed: Mar. 31, 2010

(65) Prior Publication Data

US 2010/0239156 A1    Sep. 23, 2010

Related U.S. Application Data

(63) Continuation of application No. 10/953,060, filed on Sep. 30, 2004, now Pat. No. 7,706,598.

(30) Foreign Application Priority Data

Oct. 1, 2003   (JP) ................................ 2003-343090

(51) Int. Cl.
*G06K 9/00*   (2006.01)
(52) U.S. Cl. ........ 382/145; 382/144; 382/147; 382/148; 382/149; 382/151
(58) Field of Classification Search .................. 382/145, 382/147, 148, 149, 151, 130
See application file for complete search history.

(56) References Cited

U.S. PATENT DOCUMENTS

| | | | |
|---|---|---|---|
| 4,791,586 A | 12/1988 | Maeda et al. | |
| 5,659,172 A * | 8/1997 | Wagner et al. | 250/307 |
| 5,949,901 A * | 9/1999 | Nichani et al. | 382/149 |
| 6,269,194 B1 * | 7/2001 | Nichani | 382/270 |
| 6,347,150 B1 * | 2/2002 | Hiroi et al. | 382/149 |
| 6,456,318 B1 * | 9/2002 | Noguchi | 348/87 |
| 6,512,843 B1 * | 1/2003 | Kuwabara | 382/149 |
| 6,735,745 B2 * | 5/2004 | Sarig | 382/144 |
| 6,987,873 B1 | 1/2006 | Ben-Porath et al. | |
| 7,171,038 B2 * | 1/2007 | Adler et al. | 382/149 |
| 7,706,598 B2 * | 4/2010 | Shimura | 382/145 |
| 2003/0053675 A1 * | 3/2003 | Kuwabara | 382/145 |
| 2004/0179727 A1 * | 9/2004 | Takeuchi | 382/145 |

FOREIGN PATENT DOCUMENTS

JP    61-212708    9/1986

\* cited by examiner

*Primary Examiner* — Michael A Newman

(74) *Attorney, Agent, or Firm* — McDermott Will & Emery LLP

(57) ABSTRACT

A visual inspection apparatus includes an image-data acquisition unit for acquiring plural pieces of image data A to C on an inspection target, image comparison units for comparing the image data A to C with each other thereby to create plural pieces of sign-affixed difference-image data D and E, the image data A to C being acquired by the image-data acquisition unit, difference-image comparison units for determining the difference between the sign-affixed difference-image data D and E created by the image comparison units, and a judgment unit for subjecting, to a threshold-value processing, difference data F between the difference-image data D and E, the difference data F being acquired by the difference-image comparison units, obtaining a detection sensitivity by enlarging the difference between an abnormal signal level of an image of an area where an abnormality exists from the visual inspection.

16 Claims, 3 Drawing Sheets

METHOD AND APPARATUS FOR VISUAL INSPECTION

RELATED APPLICATIONS

The present application is a Continuation of U.S. application Ser. No. 10/953,060, filed on Sep. 30, 2004, now issued as U.S. Pat. No. 7,706,598, the contents of which are hereby incorporated by reference.

BACKGROUND OF THE INVENTION

1. Field of the Invention

The present invention relates to a visual inspection method and visual inspection apparatus for inspecting an abnormality from the visual outside appearance of a target to be inspected. Here, the target to be inspected refers to, e.g., a semiconductor wafer, a photo mask, or a printed board. Also, the abnormality refers to, e.g., deformation, pattern defect, or foreign-substance mixing or adherence in fabrication processing steps of the to-be-inspected target.

2. Description of the Related Art

Conventionally, as the visual inspection method for inspecting a to-be-inspected target, there has been known the following method, for example: Namely, at first, image data is acquired while performing scanning on a semiconductor wafer on which one and the same pattern is repeatedly formed on plural chips. Next, a comparison is made between images on two chips which are adjacent to each other, thereby inspecting a defect from the visual outside appearance.

Moreover, as a method for making the comparison between the images, as is disclosed in, e.g., JP-A-61-212708, there has been already known the following method or the like: at first, after performing position alignment of the two pieces of image data, the difference therebetween is assumed. Next, difference-image data acquired is subjected to a threshold-value processing, thereby detecting the defect.

In the above-described image comparison method, detecting the abnormality on the visual outside appearance necessitates the following condition: The difference between images of an area where the abnormality exists, i.e., signal level of the defect, is larger enough as compared with the difference between images of an area where no abnormality exists, i.e., noise level of the images. In particular, as the abnormality gets smaller, the difference which occurs on the images becomes smaller because of a restriction on the resolution of an image-forming system. This results in a decrease in the detection sensitivity. On account of this situation, enhancing the detection sensitivity requires that the resolution of the image-forming system be enhanced, or that the noise level of the images be reduced.

The resolution of the image-forming system, however, is determined by wavelength of light used and performance of lenses in the case of, e.g., an image-forming optical system. Accordingly, there exists a limitation on expectation of the possible improvement. Also, the noise level of the images is determined by an image grabbing device, vibration of a stage where the to-be-inspected target is securely located at the time of grabbing the images, and further, the position alignment at the time of making the image-data comparison, and type of the to-be-inspected target. Consequently, there exists a limitation on the reduction in the noise level.

SUMMARY OF THE INVENTION

It is an object of the present invention to provide a to-be-inspected target's visual inspection method and visual inspection apparatus which make it possible to enhance the detection sensitivity by enlarging, using an image processing, the difference between the signal level of an image of an area where an abnormality exists from the visual inspection and the noise level of an image of an area where no abnormality exists therefrom.

In the present invention, in order to accomplish the above-described object, in the to-be-inspected target's visual inspection apparatus, there are provided an image-data acquisition unit for acquiring plural pieces of image data on a to-be-inspected target, an image comparison unit for creating plural pieces of sign-affixed difference-image data by making a comparison among the plural pieces of image data acquired by the image-data acquisition unit, a difference-image comparison unit for making a comparison among the plural pieces of sign-affixed difference-image data created by the image comparison unit, and a judgment unit for subjecting data to a threshold-value processing, the data being acquired by the difference-image comparison unit.

In the present invention, the above-described configuration is employed where the comparison is further made among the plural pieces of difference-image data. The employment of this configuration allows the final abnormal signal level of the image of the area where the abnormality exists to be made substantially 1.4 times larger as compared with the final noise level of the image of the area where no abnormality exists. This makes it possible to enhance the detection sensitivity by the amount.

As explained so far, according to the present invention, it becomes possible to acquire the to-be-inspected target's visual inspection method and visual inspection apparatus which make it possible to enhance the detection sensitivity by enlarging the difference between the abnormal signal level of the image of the area where the abnormality exists from the visual inspection and the noise level of the image of the area where no abnormality exists therefrom.

Other objects, features and advantages of the invention will become apparent from the following description of the embodiments of the invention taken in conjunction with the accompanying drawings.

DETAILED DESCRIPTION. OF THE EMBODIMENTS

Figure 1:
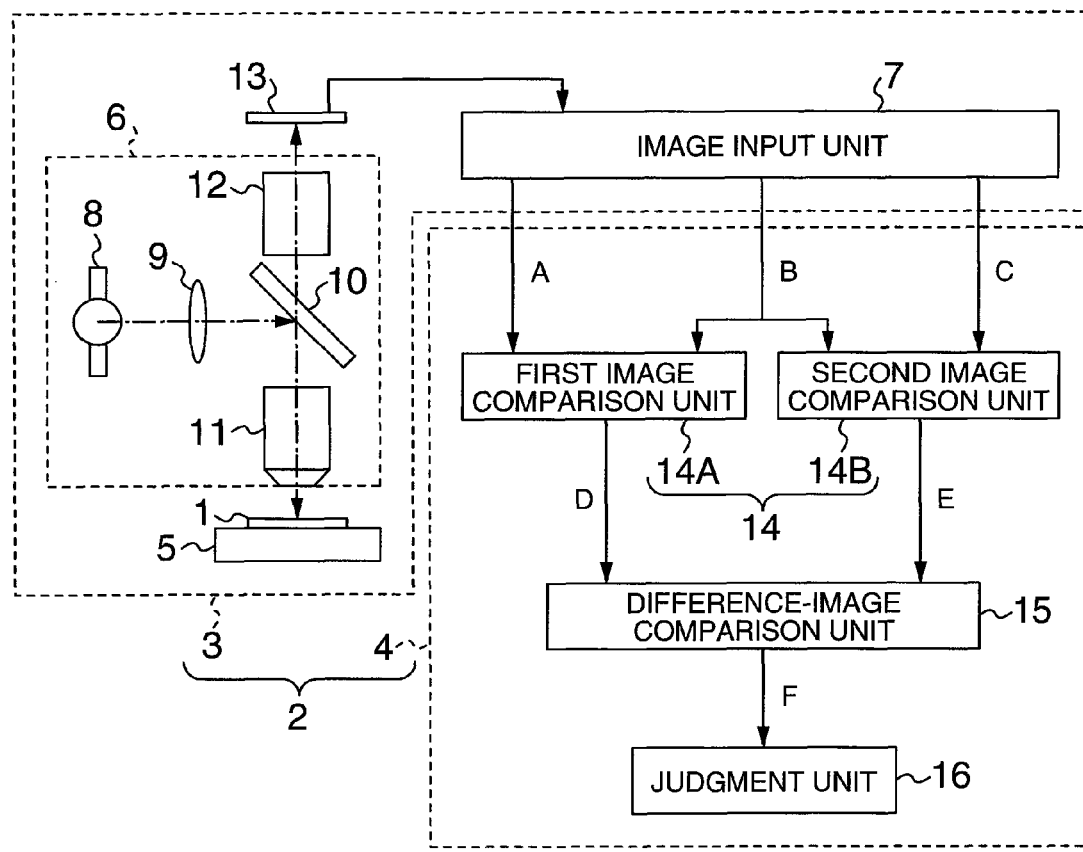
FIG. 1 is a block diagram for illustrating a first embodiment of a to-be-inspected target's visual inspection apparatus according to the present invention.
Figure 2:
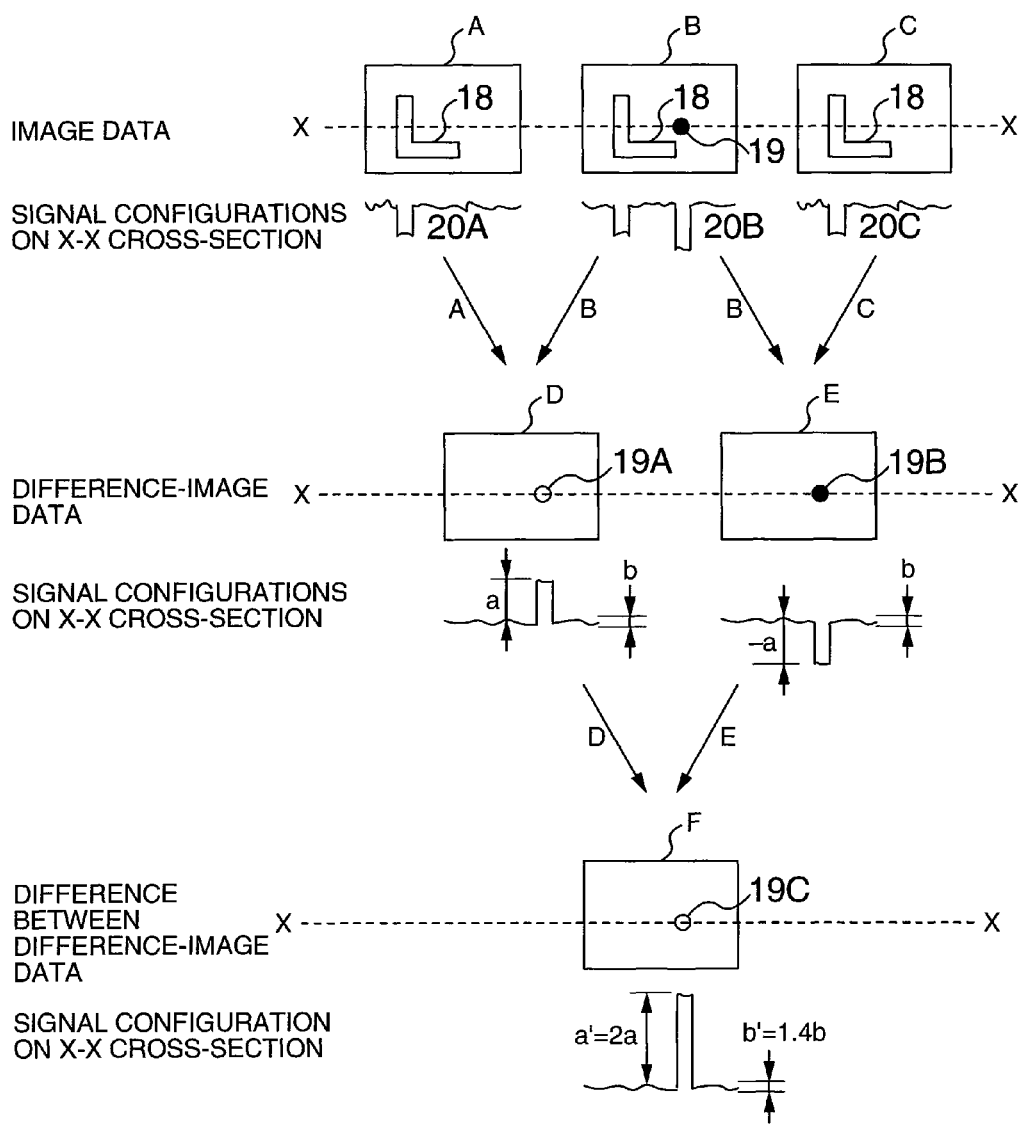
FIG. 2 is an explanatory diagram for explaining changes in image data according to FIG. 1.

Hereinafter, based on FIG. 1 to FIG. 3, the explanation will be given below concerning a first embodiment of a to-be-inspected target's visual inspection apparatus according to the present invention.

Figure 3:
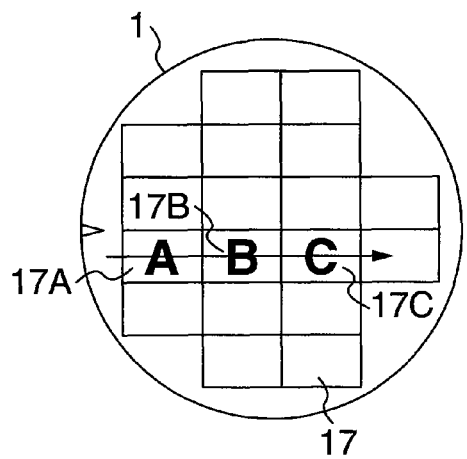
FIG. 3 is a plan view for illustrating a to-be-inspected target used in FIG. 1.

A to-be-inspected target 1 is a semiconductor wafer including, e.g., plural chips 17 on which one and the same pattern illustrated in FIG. 3 is formed. A visual inspection apparatus 2 for inspecting this to-be-inspected target 1 from the visual outside appearance is basically divided into and is configured by an image-data acquisition unit 3 for acquiring image data on the to-be-inspected target 1, and an image processing unit 4.

The image-data acquisition unit 3 includes a stage 5 for securely locating thereon the to-be-inspected target 1 and displacing the target 1 in X, Y, Z directions and a θ direction, an optical system 6 for photographing optical images of the to-be-inspected target 1 on this stage 5, and an image input unit 7 for converting, into image data, the optical images photographed by this optical system 6 and outputting the image data to the image processing unit 4.

The optical system 6 includes an illumination optical system and an image-forming optical system. The illumination optical system includes a light-source 8, an illuminating lens 9 for converging light from the light-source 8, a beam splitter 10 for guiding light emitted from the illuminating lens 9 onto the side of the to-be-inspected target 1, and an objective lens 11. The image-forming optical system includes the objective lens 11 for permitting reflected light from the to-be-inspected target 1 to pass therethrough, the beam splitter 10, an image-forming lens 12, and an image-photographing device 13 for photographing images formed by light which has passed through the image-forming lens 12.

The light-source used as the light-source 8 is incoherent light-source such as Xe lamp or Hg lamp, laser, or the like. Although, conventionally, visible-area light had been mainly used, UV or DUV (: Deep Ultraviolet)-area light has been used recently.

Also, the device used as the image-photographing device 13 is line sensor such as TDI image sensor, area sensor, or the like.

The image data photographed by the image-photographing device 13 is inputted into the image input unit 7 so as to undergo an AD conversion, then being inputted into the image processing unit 4.

The image processing unit 4 includes an image comparison unit 14 including a first image comparison unit 14A and a second image comparison unit 14B for inputting the AD-converted image data, a difference-image comparison unit 15 for inputting difference-image data outputted from the image comparison unit 14 (i.e., 14A, 14B), and a judgment unit 16 for inputting comparison data outputted from the difference-image comparison unit 15 and judging the presence or absence of an abnormality.

Next, the explanation will be given below regarding a to-be-inspected target 1's visual inspection method which uses the visual inspection apparatus 2 having the above-described configuration.

As illustrated in FIG. 3, the semiconductor wafer, i.e., the to-be-inspected target 1, is securely located on the stage 5. The plural chips 17 having the same pattern are formed on this to-be-inspected target 1. The photographing is performed while displaying the stage 5 in the arrow direction, thereby acquiring three pieces of image data A to C from respective chips 17A to 17C. Here, the data acquired by photographing the different chips 17A to 17C on the to-be-inspected target 1 have been employed as the three pieces of image data A to C, respectively. In addition, the following data may also be defined as the image data A to C: One piece of image data, image data resulting from shifting the one piece of image data by the amount of an integer multiplication of period of the repeated pattern in the image, and image data resulting from further shifting the image data by the amount of an integer multiplication of period of the repeated pattern. Moreover, data acquired by photographing three independent to-be-inspected targets 1 on one-by-one basis may also be defined as the image data A to C.

Of the image data A to C thus acquired, the one piece of image data B is outputted onto two channels. Namely, the image data A and B are inputted into the first image comparison unit 14A, and the image data B and C are inputted into the second image comparison unit 14B. Moreover, the image data A and B and the image data B and C, which have been inputted into the first image comparison unit 14A and the second image comparison unit 14B respectively, are compared with each other after position shifts of the images have been corrected. Furthermore, the differences therebetween are outputted as sign-affixed difference-image data D and E with minus signs of the differences maintained.

Moreover, the difference-image data D with a sign and E with a sign are inputted into the difference-image comparison unit 15. Here, the data D and E are further compared with each other, thereby outputting difference data F between the difference-image data D and E. Furthermore, the difference data F between the difference-image data D and E is inputted into the judgment unit 16. Here, the difference data F is subjected to a threshold-value processing, thereby judging the presence or absence of an abnormality.

Next, referring to FIG. 2, the concrete explanation will be given below concerning the reason why it becomes possible to enlarge the difference between the abnormal signal level of an image of an area where an abnormality exists from the visual inspection and the noise level of an image of an area where no abnormality exists therefrom.

In this embodiment, in the three pieces of image data A to C sent from the image input unit 7 (FIG. 1), the pattern 18 which is common thereto exists. Also, a defect area 19 exists in the image data B. The signal configurations on X-X cross-section passing through the defect area 19 of these pieces of image data A to C turn out to become configurations (20A) to (20C).

The first image comparison unit 14A (FIG. 1) subtracts the image data B from the image data A, thereby creating the difference-image data D. As a result of this subtraction, the defect area 19A has a positive pixel value a in this difference-image data D. The remaining area which does not include the defect area 19A has a random noise component b caused by influences of noise of the image-photographing device 13 (FIG. 1), vibration at the time of the photographing, and the like. Accordingly, it becomes possible to represent the S/N ratio of this difference-image data D by a/b.

Also, the second image comparison unit 14B (FIG. 1) subtracts the image data C from the image data B, thereby creating the difference-image data E. As a result, the defect area 19B has a pixel value with a minus sign −a in this difference-image data E. The noise component in the remaining area which does not include the defect area 19B is approximated as being a noise component b which is the same as the one in the difference-image data D. Consequently, it also becomes possible to represent the S/N ratio of this difference-image data E by a/b which is the same as the one in the difference-image data D.

Furthermore, the difference-image data D with the sign and E with the sign are inputted into the difference-image comparison unit 15 (FIG. 1), where the data D and E are compared with each other. At this time, the defect areas 19A and 19B have the pixel values a and −a respectively whose signs are opposite to each other. Accordingly, a pixel value a' of the defect area 19C in the difference data F above-described can be approximated as being 2a. Meanwhile, a pixel value b', which is a random noise component, in the remaining area which does not include the defect in the difference data F becomes equal to 1.4b, because there is no correlation between the difference-image data D and E.

Accordingly, the S/N ratio of the difference data F between the difference-image data D and E becomes equal to a'/b'=1.4a/b.

In this way, in the difference data F between the sign-affixed difference-image data D and E, it becomes possible to make the pixel value 1.4 times larger as compared with the random noise component. This condition, consequently, allows the enlargement of the difference between the abnormal signal level and the noise level by the amount, thereby making it possible to enhance the detection sensitivity. This, in other words, means that detecting a smaller defect becomes executable.

Figure 4:
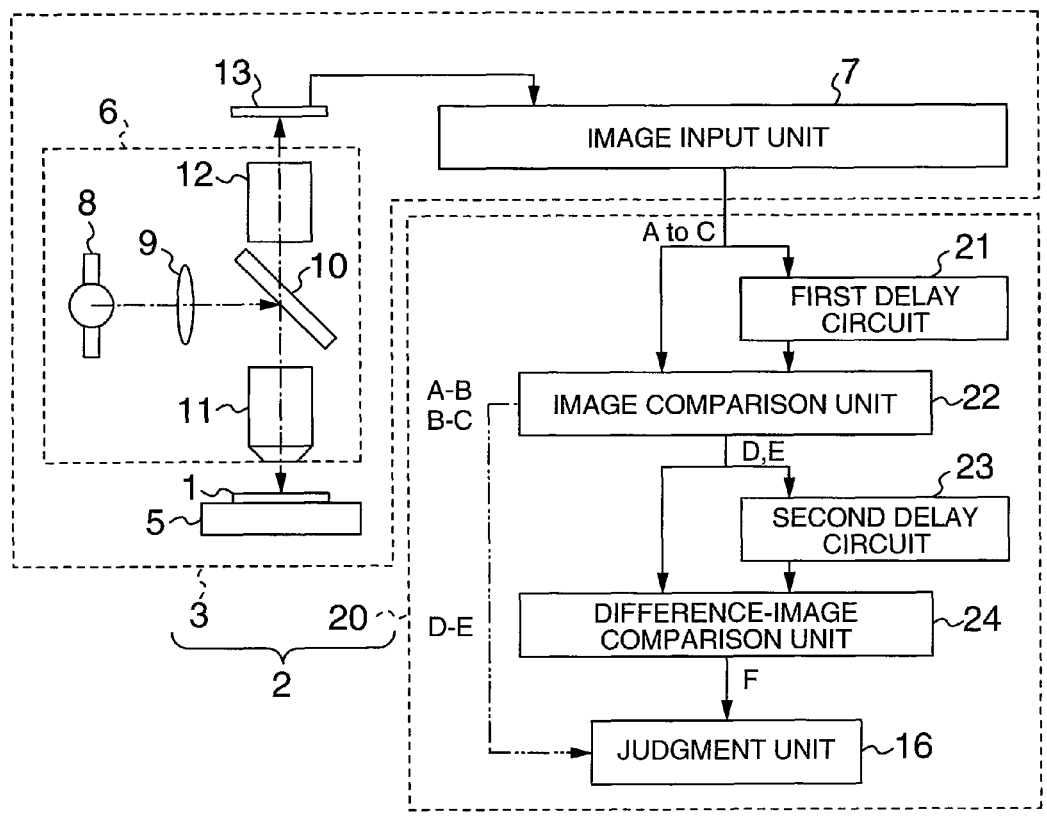
FIG. 4 is a block diagram for illustrating a second embodiment of the to-be-inspected target's visual inspection apparatus according to the present invention.

Next, based on FIG. 4, the explanation will be given below concerning a second embodiment of the to-be-inspected target's visual inspection apparatus according to the present invention.

The present embodiment is the same as the first embodiment in that the visual inspection apparatus 2 is basically divided into and is configured by the image-data acquisition unit 3 for acquiring image data on the to-be-inspected target 1, and an image processing unit 20. The present embodiment, however, differs significantly from the first embodiment in that image data are processed in a time-sequence manner in the image processing unit 20. Incidentally, the image-data acquisition unit 3 is the same as the one in the first embodiment, and thus the repeated explanation thereof will be omitted.

Namely, the image processing unit 20 into which the image data are inputted one after another from the image input unit 7 of the image-data acquisition unit 3 includes a first delay circuit 21 such as an image memory for inputting the image data outputted from the image input unit 7, and an image comparison unit 22 for inputting and making a comparison between the image data outputted from the image input unit 7 and the image data outputted via the first delay circuit 21. In the first delay circuit 21, by the time equivalent to a time needed for acquiring one piece of image data, a timing with which the image data is outputted is delayed.

In the image comparison unit 22, position alignment is performed between the image data which are inputted into the first delay circuit 21 in advance and are outputted in a state of being delayed and the image data which are newly inputted from the image input unit 7. After that, the differences between both of the image data are determined, thereby outputting difference-image data. The difference-image data have signs of the differences. Incidentally, the position alignment data between both of the image data is outputted in a state of being added to the difference-image data.

Also, the image processing unit 20 includes a second delay circuit 23 for inputting the sign-affixed difference-image data outputted from the image comparison unit 22, a difference-image comparison unit 24 for inputting and calculating the difference between the sign-affixed difference-image data outputted from the image comparison unit 22 and the sign-affixed difference-image data outputted via the second delay circuit 23, and the judgment unit 16 for subjecting, to a threshold-value processing, the difference data between the sign-affixed difference-image data outputted from the difference-image comparison unit 24, and thereby judging the presence or absence of an abnormality.

Next, the explanation will be given below regarding an inspection method performed by the visual inspection apparatus 2 having the above-described configuration.

The semiconductor wafer, i.e., the to-be-inspected target 1 on which the plural chips 17 (FIG. 3) are formed, is securely located on the stage 5. Then, the stage 5 is displaced along the scan line, thereby acquiring the images. As a result of this, the image data A, B, and C on the chips 17A, 17B, and 17C adjacent to each other are acquired in time sequence.

In the image processing unit 20, the image data A on the chip 17A acquired at first is inputted into the first delay circuit 21, and also is inputted into the image comparison unit 22. Subsequently, the image data B on the chip 17B acquired next is similarly inputted into the first delay circuit 21, and also is inputted into the image comparison unit 22. At this time, in the image comparison unit 22, a comparison is made between the image data B on the chip 17B and the image data A on the chip 17A which has been inputted into the first delay circuit 21 in advance.

Concretely, in the image comparison unit 22, after position shift between the image data A on the chip 17A and the image data B on the chip 17B has been corrected, the difference between both of the image data A and B is determined as the difference-image data D. Also, the data on the difference as well as the position alignment data are added to the difference-image data D determined in this way. This difference-image data D is inputted into the next units, i.e., the second delay circuit 23 and the difference-image comparison unit 24.

Moreover, the image data C on the chip 17C acquired is inputted into the first delay circuit 21, and also is inputted into the image comparison unit 22. In the image comparison unit 22, a comparison is made between the image data C on the chip 17C inputted therein and the image data B on the chip 17B which has been inputted into the first delay circuit 21 in advance. Moreover, after position shift between the image data B on the chip 17B and the image data C on the chip 17C has been corrected, the difference between both of the image data B and C is determined as the difference-image data E. Also, the data on the difference as well as the position alignment data are added to the difference-image data E determined in this way. This difference-image data E is inputted into the next units, i.e., the second delay circuit 23 and the difference-image comparison unit 24.

In the difference-image comparison unit 24, a comparison is made between the sign-affixed difference-image data E and the sign-affixed difference-image data D which has been inputted therein in advance via the second delay circuit 23. Furthermore, after position shift between the sign-affixed difference-image data D and E has been corrected, the difference data F between the sign-affixed difference-image data D and E is determined.

The difference data F between the sign-affixed difference-image data D and E determined in this way is inputted into the judgment unit 16. Here, the difference data F is subjected to a threshold-value processing, thereby judging the presence or absence of an abnormality.

Incidentally, depending on the type of the to-be-inspected target 1, the comparison made in the image comparison unit 22 is sufficient to be able to judge whether or not a defect area exists. In this case, as illustrated by the two-point chain line, the output from the image comparison unit 22 may be directly inputted into the judgment unit 16. If, here, the direct inputting prevents execution of the judgment, the output may be inputted into the judgment unit 16 after the comparison in the difference-image comparison unit 24 has been made.

As having been explained so far, in the present invention, at least the three different pieces of image data are compared with each other, thereby creating at least the two different pieces of sign-affixed difference-image data. Moreover, the difference data between the two different pieces of sign-affixed difference-image data is subjected to a threshold-value processing. This procedure allows the enlargement of the difference between the abnormal signal level and the noise level, thereby making it possible to enhance the detection sensitivity.

By the way, although, in the above-described to-be-inspected target's visual inspection apparatus, the example has been indicated where the optical image is acquired and applied, it is also allowable to perform the inspection by utilizing images acquired using an electron beam.

Further, although, in the respective embodiments according to the present invention, the image data are processed by using the hardware, it is also allowable to perform a part or the whole of the image data processing by using software.

In addition to this, in the present embodiments, in the image comparison units 14 and 22, the data resulting from correcting and position-aligning the image shift between the image data A-B and the one between the image data B-C are signed, then being affixed to the difference-image data D and E and inputted into the difference-image comparison units 15 and 24. However, inputting the position alignment data into the difference-image comparison units 15 and 24 is not absolutely necessary. For example, in the embodiment illustrated in FIG. 1, if, when performing the position alignment, image positions of the image data A and C are adjusted with the image data B selected as the criterion, there exists no image shift between the difference-image data D and E. Consequently, there exists no necessity for inputting the position alignment data into the difference-image comparison units 15 and 24, and performing the position alignment in the difference-image comparison units 15 and 24.

Even further, in the above-described respective embodiments, the example has been indicated where the image data A to C on the chips 17 are compared with each other. The present invention, however, is also applicable to the following case (i.e., cell-to-cell comparison): Namely, in an area (i.e., cell area) where the same configuration is formed repeatedly within the same chip 17, images are compared with each other in such a manner that the image data are shifted by the amount of a constant multiplication of the repeated period.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus for inspecting for an abnormality of a substrate having a pattern formed thereon comprising:
   an illumination system which irradiates said substrate with a light;
   a detection system which detects a light from said substrate;
   a first processor which makes a first image, a second image and a third image of a detection result of said detection system;
   a second processor which makes a first signed subtraction image by subtracting said second image from said first image;
   a third processor which makes a second signed subtraction image by subtracting said third image from said second image;
   a fourth processor which makes a subtraction image of said first signed subtraction image, and said second signed subtraction image by subtracting said second signed subtraction image from said first signed subtraction image; and
   a fifth processor which inspects said substrate by threshold-value processing of said subtraction image obtained by said fourth processor, wherein:
   a sign of an abnormal area in said first signed subtraction image has a reverse sign of a corresponding abnormal area in said second signed subtraction image, and
   a first coordinate of said abnormal area in said first signed subtraction image is substantially same as a second coordinate of said abnormal area in said second signed subtraction image.

2. The inspection apparatus according to claim 1, wherein at least one of said second processor, said third processor, and said fourth processor, includes a time-delay memory.

3. An inspection apparatus for inspecting for an abnormality of a substrate having a pattern formed thereon comprising:
   an illumination system which irradiates said substrate with a light;
   a detection system which detects a light from said substrate;
   a first processor which makes a first data, a second data, and a third data of a detection result of said detection system;
   a second processor which makes a first signed subtraction data by subtracting said second data from said first data;
   a third processor which makes a second signed subtraction data by subtracting said third data from said second data;
   a fourth processor which makes a subtraction data of said first signed subtraction data, and second signed subtraction data by subtracting said second signed subtraction data from said first signed subtraction data; and
   a fifth processor which inspects said substrate by threshold-value processing of said subtraction data obtained by said fourth processor, wherein:
   a sign of an abnormal area in said first signed subtraction data has a reverse sign of a corresponding abnormal area in said second signed subtraction data,
   a first coordinate of said abnormal area in said first signed subtraction data is substantially same as a second coordinate of said abnormal area in said second signed subtraction data.

4. The inspection apparatus according to claim 3, wherein at least one of said second processor, said third processor, and said fourth processor, includes a time-delay-memory.

5. An inspection method for inspecting for an abnormality of a substrate having a pattern formed thereon comprising:
   irradiating said substrate with a light by an illumination system;
   detecting a light from said substrate by a detection system;
   making a first image, a second image, and a third image of a detection result of said detection by a first processor;
   making a first signed subtraction image by subtracting said second image from said first image with a second processor;
   making a second signed subtraction image by subtracting said third image from said second image with a third processor;
   making a subtraction image of said first signed subtraction image, and said second signed subtraction image by subtracting said second signed subtraction image from said first signed subtraction image with a fourth processor; and
   inspecting said substrate by threshold-value processing, which uses said subtraction image obtained by said fourth processor, by a fifth processor, wherein:
   a sign of an abnormal area in said first signed subtraction image has a reverse sign of a corresponding abnormal area in said second signed subtraction image, a first coordinate of said abnormal area in said first signed subtraction image is substantially same as a second coordinate of said abnormal area in said second signed subtraction image.

6. The inspection method according to claim 5, wherein at least one of said first signed subtraction image, said second signed subtraction image, and said subtraction image obtained by said fourth processor, is processed in a time-sequence manner.

7. An inspection method for inspecting for an abnormality of a substrate having a pattern formed thereon comprising:

irradiating said substrate with a light by an illumination system;

detecting a light from said substrate by a detection system;

making a first data, a second data, and a third data of detection result of said detection by a first processor;

making a first signed subtraction data by subtracting said second data from said first data with a second processor;

making a second signed subtraction data by subtracting said third data from said second data with a third processor;

making a subtraction data of said first signed subtraction data, and said second signed subtraction data by subtracting said second signed subtraction data from said first signed subtraction data with a fourth processor; and inspecting said substrate by threshold-value processing of said subtraction data obtained by said fourth processor by a fifth processor, wherein:

a sign of an abnormal area in said first signed subtraction data has a reverse sign of a corresponding abnormal area in said second signed subtraction data, a first coordinate of said abnormal area in said first signed subtraction data is substantially same as a second coordinate of said abnormal area in said second signed subtraction data.

8. The inspection method according to claim 7, wherein at least one of said first signed subtraction data, said second signed subtraction data, and said subtraction data obtained by said fourth processor, is processed in a time-sequence manner.

9. The inspection apparatus according to claim 1, wherein the fourth processor changes the first coordinate to be same as the second coordinate.

10. The inspection apparatus according to claim 1, wherein the fourth processor changes the second coordinate to be same as the first coordinate.

11. The inspection apparatus according to claim 3, wherein the fourth processor changes the first coordinate to be same as the second coordinate.

12. The inspection apparatus according to claim 3, wherein the fourth processor changes the second coordinate to be same as the first coordinate.

13. The inspection method according to claim 5, wherein the fourth processor changes the first coordinate to be same as the second coordinate.

14. The inspection method according to claim 5, wherein the fourth processor changes the second coordinate to be same as the first coordinate.

15. The inspection method according to claim 7, wherein the fourth processor changes the first coordinate to be same as the second coordinate.

16. The inspection method according to claim 7, wherein the fourth processor changes the second coordinate to be same as the first coordinate.

* * * * *